United States Patent [19]
Yoshida et al.

[11] Patent Number: 5,589,165
[45] Date of Patent: Dec. 31, 1996

[54] COSMETIC

[75] Inventors: Masashi Yoshida; Tomiyuki Nanba; Keiichi Uehara; Osamu Sakurai; Hideki Takahashi; Hiroshi Fukui, all of Yokohama, Japan

[73] Assignee: Shiseido Co., Ltd., Tokyo, Japan

[21] Appl. No.: 361,598

[22] Filed: Dec. 22, 1994

[30] Foreign Application Priority Data

Dec. 28, 1993 [JP] Japan .................. 5-353169

[51] Int. Cl.$^6$ .................. A61K 31/74; A61K 7/027
[52] U.S. Cl. .................. 424/78.03; 424/59; 424/64; 424/70.7; 424/70.12; 514/845; 514/846; 514/847
[58] Field of Search .................. 424/70.12, 401, 424/78.03, 69, DIG. 2, 59, 64, 70.7; 523/213; 514/845, 846, 847

[56] References Cited

U.S. PATENT DOCUMENTS

| | | | |
|---|---|---|---|
| 4,036,807 | 7/1977 | Atherton | 523/213 |
| 4,386,170 | 5/1983 | Monroe | 523/210 |
| 5,061,740 | 10/1991 | Inomata | 523/213 |

*Primary Examiner*—Sallie M. Gardner
*Attorney, Agent, or Firm*—Townsend & Banta

[57] ABSTRACT

A cosmetic with good water resistance, perspiration resistance and oil resistance, as well as long lasting cosmetic effects, which characteristically containing an organofluorated modified silicone resin comprising units (1), (2) and (3) shown below:

(1) $R_3SiO_{1/2}$ units
(2) $SiO_2$ units
(3) $Rf_2SiO$ unit and/or $RfRSiO$ units in which R denotes a hydrocarbon group with a carbon number of 1–6 or a phenyl group, and Rf denotes $-(CH_2)_m C_n F_{2n+1}$, m is an integer 2–4, and n is an integer 1–12.

4 Claims, No Drawings

COSMETIC

FIELD OF THE INVENTION

The present invention relates to a cosmetic which has good water resistance, perspiration resistance and oil resistance, as well as long lasting cosmetic effects and superior stability without giving a pressed feeling on the skin.

BACKGROUND OF THE INVENTION

Description of Related Art

Cosmetics can be wrinkled or washed off by sevum, perspiration or oil from other cosmetics, i.e. the makeup can be compromised. In particular, compromised makeup in the summer with high temperatures and high humidity has been a common nuisance to women, and thus improvements have been desired.

Blending in silicone resins is one way to prevent compromised makeup, such as is disclosed in Japanese unexamined patent publication Tokkai Sho 61-187708. However, since this is a silicone resin which is prepared by hydrolysis of organic trichlorosilane and organic dichlorosilane, followed by condensation and hardening by means of crosslinking, the low molecular weight silicone resin is sticky and compromised makeup cannot be sufficiently prevented.

On the other hand, if the degree of polymerization was raised and a three-dimensional network structure was formed to minimize stickiness and achieve sufficient prevention of compromised makeup, then there were problems in that compatibility with other cosmetic oil components and silicone oils and such was reduced and eventually it became insoluble, resulting in instability, as well as the fact that crosslinking polymerization occurs in the long run, resulting in compromised product stability particularly at higher temperatures. Tokkai Sho 61-65809 used a silicone resin comprising $R_3SiO_{1/2}$ units and there were therefore problems in that when this makeup cosmetic was applied on the skin, the silicone coating film formed on the skin was too hard and gives a pressing feeling on the skin, and also the cosmetic effect did not last long.

Observing such problems, the inventors began researching for the purpose of obtaining a cosmetic superior in preventing compromised makeup, and discovered that such a cosmetic can be obtained by using an organofluorated modified silicone resin with a specific structure, and completed the present invention based on this finding.

SUMMARY OF THE INVENTION

That is, the present invention is a cosmetic characteristically containing an organofluorated modified silicone resin comprising units (1), (2) and (3) shown below:

(1) $R_3SiO_{1/2}$ units
(2) $SiO_2$ units
(3) $Rf_2SiO$ units and/or RfRSiO units R denotes a hydrocarbon group with a carbon number of 1–6 or a phenyl group, and Rf denotes $-(CH_2)_mC_nF_{2n+1}$, m is an integer 2–4, and n is an integer 1–12.

DETAILED DESCRIPTION OF THE INVENTION

The organofluorated modified silicone resin used in the present invention can easily be obtained by mixing corresponding known silanes and diluting them with solvents such as toluene and hexane, followed by hydrolysis and heated polymerization. For the $SiO_2$ unit, water glass, instead of silanes, can also be used to obtain similar silicone resins.

To give some representative examples: $Me_3SiCl$ or $Me_3SiOMe$ can be used for the known silanes to produce (1) $R_3SiO_{1/2}$ units as described above; $Si(OMe)_4$ and/or $Si(OEt)_4$ can be used for the known silanes to produce (2) $SiO_2$ units as described above; and $C_nF_{2n+1}CH_2CH_2SiMeCl_2$ and/or $(C_nF_{2n+1}CH_2CH_2)_2SiCl_2$ (n is an integer 1–12) can be the known silanes to produce (3) $Rf_2SiO$ units and/or RfRSiO units. First these are dissolved in toluene and an acid catalyst(s) is added to them, followed by heated stirring to form the silicone resin backbone by means of hydrolysis. Solvent toluene is added to the mixture, and, after aging and neutralization, azeotropic dehydration and filtration are conducted. After the solvent is removed, an organofluorated modified silicone resin comprising units (1), (2) and (3) as described above is obtained in a powder form.

While the degree of polymerization of the organofluorated modified silicone resin used in the present invention can be adjusted depending on the target usage, a weight average molecular weight of 1,000–20,000 is preferable.

The blend ratio of the organofluorated modified silicone resin used in the present invention is not limited in particular, but 5–60 wt % of the total cosmetic of the present invention is preferable, and more preferably 8–30 wt %. If it is less than 5 wt %, then the effect of the resin will not be significant. If it is more than 60 wt %, then stickiness will become significant and ease of use will be drastically compromised.

The organofluorated modified silicone resin used in the present invention can be blended as is in a cosmetic. However, generally speaking, it is preferable to use a volatile silicone oil represented by the general formula 1 or 2 shown below for the sake of facilitating the manufacturing process of the cosmetic.

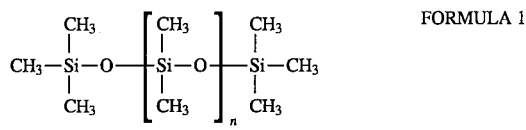

FORMULA 1

(In this formula, n denotes an integer 0–5.)

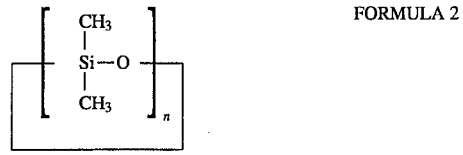

FORMULA 2

(In this formula, n denotes an integer 3–7.)

In addition to the essential components described above, other components which are usually blended into cosmetics, including oils, resins, silicone rubber, moisture retaining agents, antioxidants, surface active agents, preservatives, anti-inflammatories, ultraviolet light adsorbents, drugs such as vitamins and hormones, sequestering agents, viscosity adjusting agents and perfumes, can be blended into the cosmetic of the present invention.

For the oil, various hydrocarbons, higher fatty acids, fats and oils, esters, higher alcohols, waxes, silicone oils and fluorocarbon oils including squalene, liquid paraffin, vaseline, microcrystalline wax, ozokerite, ceresin, myristic acid, palmitic acid, stearic acid, oleic acid, isostearic acid, cetyl alcohol, hexadecyl alcohol, oleyl alcohol, cetyl-2-ethyl hexanoate, 2-ethylhexyl palmitate, 2-octyldodecyl myristate, 2-octyldodecylgum ester, neopentylglycol-2-ethyl hexanoate, isooctyric acid triglyceride, 2-octyldodecyl oleate, isopropyl myristate, isostearic acid triglyceride, coconut oil fatty acid triglyceride, olive oil, avocado oil, bees wax, myristyl myristate, mink oil, lanolin, dimethylpolysiloxane, ring dimethylpolysiloxane, methylphenylpolysiloxane, silicone resins, polyether modified silicone, amino modified silicone, etc. can be used.

For the powder, any powder which is commonly blended into cosmetics can be blended into the present invention. Examples are: pearl pigments such as talc, muscovite, synthetic mica, phlogopite, lepidolite, black mica, lithia mica, sericite, vermiculite, kaolin, titanium dioxide, titanium oxide-coated mica, titanium oxide-coated talc, titanium oxide-coated oxybismuth chloride, fish scale flakes and colored titanium oxide-coated mica; metal powder pigments such as aluminum powder and copper powder; inorganic red pigments such as iron oxide (red iron oxide) and iron titanate; inorganic brown pigments such as gamma-iron oxide; inorganic yellow pigments such as yellow iron oxide and loess; inorganic black pigments such as black iron oxide and carbon black; inorganic purple pigments such as mango violet and cobalt violet; inorganic green pigments such as chromium oxide, chromium hydroxide and cobalt titanate; inorganic blue pigments such as ultramarine blue and Berlin blue; zinc white, bentonite, barium sulfate, rectal soap, silious earth, aluminum silicate, calcium silicate, barium silicate, magnesium silicate, stronthium silicate, rectal tungstates, calcium carbonate, magnesium carbonate, chromium oxide, chromium hydroxide, carbon black, alumina, hydoxyapatite, boron nitride, silica, nylon powder, silicone powder, zeolite, benzoguanamine powder, ethylene tetrafluoride powder, polyamide powder, polyester powder, polyethylene powder, polypropylene powder, polystyrene powder, cellulose powder; organic pigments such as red 201, red 202, red 204, red 205, red 220, red 226, red 228, red 405, orange 203, orange 204, yellow 205, yellow 401 and blue 404; organic pigments such as zirconium, barium or aluminum lakes of red 3. red 104, red 106, red 227, red 230, red 401, red 505, orange 205, yellow 4, yellow 5, yellow 202, yellow 203, green 3 and blue 1; and natural colors such as chlorophyll and beta-carotene.

Examples of the ultraviolet light absorbent are: the benzoic acid type such as para-amino benzoate (hereafter abbreviated as "PABA"), glyceryl PABA, n-dimethyl PABA butylether and octyldimethyl PABA; the salicylic acid type such as amino salicylate; and the cinnamic acid type such as octyl cinnamate, ethyl-2,4-diisopropyl cinnamate and octylmethoxy cinnamate; the benzophenone type such as 2,4-dihydroxybenzophenone and 2-hydroxy-4-methoxybenzophenone.

Needless to say, it is also possible to apply an emulsification technique by using purified water, water soluble components and appropriate surface active agents to make an oil-in-water type or water-in-oil type emulsified composition such that the water repellency is not lost.

EXAMPLES

Details of the present invention are described below by referring to examples. However, the present invention is not limited to these examples. The blend ratios are expressed in wt % units.

Example 1

|  | Oil-type foundation |
| --- | --- |
| (1) Kaolin | 25% |
| (2) Titanium dioxide | 15 |
| (3) Iron oxide | 3 |
| (4) Microcrystalline wax | 4 |
| (5) Liquid paraffin | 5 |
| (6) Sorbitan sesquioleate | 1 |
| (7) Octamethylcyclotetrasiloxane | Balance |
| (8) Organofluorated modified silicone resin comprising: $(CH_3)_3SiO_{1/2}/(CF_3CH_2CH_2)_2SiO/SiO_2$ wherein the content of the $(CF_3CH_2CH_2)_2SiO$ unit is 11 wt % and the weight average molecular weight is 11,100 | 10 |
| (9) Perfume | Appropriate amount |

Preparation Process (4) through (8) were stirred and dissolved at 70°–80° C., and (1) through (3) were added to the mixture and dispersed. After deaeration, (9) was added and the product was poured into a container to obtain the oil-type foundation.

The oil-type foundation of Example 1 was a foundation with superior water resistance, oil resistance and perspiration resistance which was less susceptible to becoming compromised makeup. It did not develop cracks over time, did not cause a pressing feeling on the skin, and felt refreshing when used. After this product was stored at 50° C. for 1 month, it was stable without any aggregation or separation.

Comparative Example 1

|  | Oil-type foundation |
| --- | --- |
| (1) Kaolin | 25% |
| (2) Titanium dioxide | 15 |
| (3) Spherical nylon | 3 |
| (4) Iron oxide | 3 |
| (5) Microcrystalline wax | 4 |
| (6) Liquid paraffin | 5 |
| (7) Sorbitan sesquioleate | 1 |
| (8) Octamethylcyclotetrasiloxane | Balance |
| (9) Organic silicone resin comprising: $(CH_3)_3iO_{1/2}$ units and $SiO_2$ units with a blend ratio of 1.5:1 whose average molecular weight is 4,000 | 10 |
| (10) Perfume | Appropriate amount |

Preparation Process (5) through (9) were stirred and dissolved at 70°–80° C., and (1) through (4) were added to the mixture and dispersed. After deaeration, (10) was added and the product was filled in a container to obtain the oil-type foundation.

Example 1 and Comparative Example 1 were evaluated as follows

Filter paper was wetted with water or squalene was tapped 10 times from above with vertical strokes using a nylon plate on which Example 1 or Comparative Example 1 had been applied and dried. After the tapping was completed, the amount of the sample transferred from the nylon plate to the filter paper was visually evaluated based on the shade of the color.

| Evaluation | |
|---|---|
| 1 | Not transferred at all. |
| 2 | Small amount is transferred. |
| 3 | Significant amount is transferred. |

The results are shown in Table 1 as the average of a total of 5 experiments.

TABLE 1

| | Water | Squalene |
|---|---|---|
| Example 1 | 0.5 | 0.5 |
| Comparative Example 1 | 2.2 | 2.8 |

Compared with the Comparative Example, which is a conventional oil type foundation with long lasting cosmetic effects, Example 1 comes off with more difficulty when exposed to water or squalene. This means it is a cosmetic with superior water resistance and oil resistance as well as long lasting cosmetic effects.

Example 2

| | Liquid lip color |
|---|---|
| (1) Dimethylpolysiloxane 0.65 cs (n = 0 in Formula 1) | 25% |
| (2) Dimethylpolysiloxane 2.0 cs (n = 3 in Formula 1) | 25 |
| (3) Organofluorated modified silicone resin comprising: $(CH_3)_3SiO_{1/2}/(CF_3CH_2CH_2)_2SiO/SiO_2$ wherein the content of the $(CF_3CH_2CH_2)_2SiO$ unit is 11 wt % and the weight average molecular weight is 11,100 | 30 |
| (4) Glyceryl triisostearate | 10 |
| (5) Red 226 | 10 |
| (6) Perfume | Appropriate amount |

Preparation Process (1) through (3) were stirred and dissolved at 70°–80° C., and (4) and (5), separately treated with a roller, were added to the mixture and dispersed. After deaeration, (6) was added to obtain the liquid lip color.

The liquid lip color of Example 2 had superior water resistance, oil resistance and perspiration resistance and was less susceptible to compromised makeup due to adhesion to a glass, for example. Also, it felt refreshing when used. After this product was stored at 50° C. for 1 month, it was stable without any aggregation, separation or increased viscosity.

Example 3

| | Mascara |
|---|---|
| (1) Dimethylpolysiloxane 1.5 cs (n = 2 in Formula 1) | 4.5% |
| (2) Octamethylcyclotetrasiloxane (n = 4 in Formula 2) | 20 |
| (3) Organofluorated modified silicone resin comprising: $(CH_3)_3SiO_{1/2}/(CF_3CH_2CH_2)_2SiO/SiO_2$ wherein the content of the $(CF_3CH_2CH_2)2SiO$ unit is 5 wt % and the weight average molecular weight is 11,100 | 60 |
| (4) Black iron oxide | 15 |
| (5) POE (20) sorbitan monolaurate | 0.5 |
| (6) Perfume | Appropriate amount |

Preparation Process (1) through (3) were stirred and dissolved at 70°–80° C., and (4) and (5) were added to the mixture and dispersed. After deaeration, (6) was added to obtain the liquid lip color.

The mascara of Example 3 was less susceptible to compromised makeup due to tearing and such, and did not adhere to eyelids. After this product was stored at 50° C. for 1 month, it was stable without any aggregation, separation or increased viscosity.

Example 4

| | Pre-makeup |
|---|---|
| (1) Silicone-treated kaolin | 10% |
| (2) Silicone-treated titanium dioxide | 5 |
| (3) Silicone-treated red iron oxide | 0.3 |
| (4) Silicone-treated yellow iron oxide | 0.2 |
| (5) Methylphenylpolysiloxane (n = 100) | 20 |
| (6) Dimethylpolysiloxane 2 cs (n = 3 in Formula 1) | 10 |
| (7) Solid paraffine | 5 |
| (8) Microcrystalline wax | 4 |
| (9) Sorbitan sesquioleate | 1 |
| (10) Orgganofluorated modified silicone resin comprising $(CH_3)_3SiO_{1/2}/(CF_3CH_2CH_2)_2SiO/SiO_2$ wherein the content of the $(CF_3CH_2CH_2)_2SiO$ unit is 20 wt % and the weight average molecular weight is 11,100 | 2 |
| (11) Decamethylcyclopentasiloxane (n = 5 in Formula 2) | 24.5 |
| (12) Perfume | Appropreate amount |

Preparation Process (1) through (4) were mixed and crushed. Separately, (5) through (11) were mixed and dissolved at 70°–80° C. The two mixtures were stirred and mixed. After deaeration, (12) was added to obtain the pre-makeup.

The pre-makeup of Example 4 had the effect of improving the applicability of the makeup cosmetic applied on top of it, as well as suppressing compromised makeup. After this product was stored at 50° C. for 1 month, it was stable without any aggregation, separation or increased viscosity.

Example 5

| | Hand cream |
|---|---|
| (1) Octamethylcyclotetrasiloxane | 15% |
| (2) Organofluroated modified silicone resin comprising $(CH_3)_3SiO_{1/2}/(CF_3CH_2CH_2)SiO/SiO_2$ wherein the content of the $(CF_3CH_2CH_2)_2SiO$ unit is 11 wt % and the weight average | 65 |

-continued

| | Hand cream |
|---|---|
| molecular weight is 11,100 | |
| (3) Microcrystalline wax | 5 |
| (4) Liquid paraffin | 15 |

Preparation Process (1) through (4) were mixed and dissolved at 70°–80° C., and cooled to obtain the hand cream.

Example 5 felt refreshing when used and exhibited skin protecting action for a long duration of time. It was also superior in water resistance, i.e. it had excellent water repellency even after washing with soap.

Example 6

| | Sunscreen Cosmetic (oil type) |
|---|---|
| (1) Decamethylcyclopentasiloxane | 48.0% |
| (2) Dimethylpolysiloxane 10 cs | 20.0 |
| (3) Organofluorated modified silicone resin comprising $(CH_3)_3SiO_{1/2}/(CF_3CH_2CH_2)_2SiO/SiO_2$ wherein the content of the $(CF_3CH_2CH_2)_2SiO$ unit is 11 wt % and the weight average molecular weight is 11,100 | 20 |
| (4) Paramethoxy-2-ethylhexyl cinnamate | 2.0 |

Preparation Process (1) through (5) were mixed and thoroughly dissolved and then filtered to obtain the sunscreen cosmetic.

Example 7

| | Sunscreen cosmetic (W/O cream) |
|---|---|
| (1) Octamethylcyclotetrasiloxane | 28% |
| (2) Organofluorated modified silicone resin comprising $(CH_3)_3SiO_{1/2}/(CF_3CH_2CH_2)_2SiO/SiO_2$ wherein the content of the $(CF_3CH_2CH_2)_2SiO$ unit is 11 wt % and the weight average molecular weight is 11,100 | 10 |
| (3) Dimethylpolysiloxane (2,500,000 cs at 25° C.) | 3.0 |
| (4) Liquid paraffin | 5.0 |
| (5) 4-methoxy-4'-t-butyldibenzoylmethane | 1.5 |
| (6) Polyether modified silicone (400 cs at 25° C.) (Polyoxyethylene group content 20 wt %) | 6.0 |
| (7) Purified water | 38.1 |
| (8) L-sodium glutamate | 3.0 |
| (9) 1,3-butyleneglycol | 5.0 |
| (10) Preservative | 0.2 |
| (11) Perfume | 0.2 |

Preparation Process (1) through (6) were mixed, heated, dissolved and the temperature of the mixture maintained at 70° C. to obtain the oil phase. Separately, (7) through (10) were heated, dissolved and the temperature of the mixture maintained at 70° C. to obtain the water phase. The water phase was added to the oil phase and the resulting mixture was thoroughly emulsified by an emulsifier. The emulsified product was stirred while being cooled. When the temperature reached 35° C. or lower, the product was poured into a container and left to stand until hard.

Comparative Example 2

The preparation process was conducted in the same manner as Example 7 except for the fact that an organic silicone resin comprising $(CH_3)_3SiO_{1/2}$ units and $SiO_2$ units with a blend ratio of 0.8 : 1 and an average molecular weight of approximately 10,000 was used instead of (2) to obtain Comparative Example 2.

Comparison Testing

Twenty specialized panelists applied Example 7 on one arm and Comparative Example 2 on the other and did outdoor exercise for 2 hours, and then evaluated the physical sensations. The results are shown below.

TABLE 2

| Symptom | Example 7 | Comparative Example 2 |
|---|---|---|
| Skin flush | ○ | Δ |
| Erythema | ○ | Δ |

The symbols in the table denote the following:
O: 5–9 panelists judged they developed the symptom.
Δ: 10–14 panelists judged they developed the symptom.
X: 15–20 panelists judged they developed the symptom.

As clearly shown in Table 1, the present invention has superior sevum resistance and perspiration resistance, and therefore has a long lasting sunburn prevention effect.

Example 8

| | Sunscreen cosmetic (W/O cream) |
|---|---|
| (1) Paramethoxy-2-ethylhexyl cinnamate | 5.0% |
| (2) 4-methoxy-4'-t-butyldibenzolylmethane | 2.0 |
| (3) Di-para-methoxycinnamic acid monoethyl hexyl acid glyceryl | 2.0 |
| (4) Vaseline | 2.0 |
| (5) Organofluorated modified silicone resin comprising $(CH_3)_3SiO_{1/2}/(CF_3CH_2CH_2)_2SiO/SiO_2$ wherein the content of the $(CF_3CH_2CH_2)_2SiO$ unit is 11 wt % and the weight average molecular weight is 11,100 | 15.0 |
| (6) Decamethylcyclopentasiloxane | 21.0 |
| (7) Dimethylpolysiloxane (molecular weight approximately 300,00000) | 8.0 |
| (8) Polyoxyalkylene modified organopolysiloxane | 3.5 |
| (9) 2-hydroxy-4-methyoxybenzophenone | 1.0 |
| (10) Distearyldimethylanmmonium chloride | 1.2 |
| (11) Perfume | Appropriate amount |
| (12) Ion exchange water | 20.0 |
| (13) Fine particle titanium oxide (average particle size 10–40 micrometers) | 7.0 |
| (14) Colored pigment | 0.5 |
| (15) Glycerine | 5.0 |
| (16) 1,3-butyeneglycol | 5.0 |
| (17) Veegum (from Vanderbilt) | 1.8 |

Preparation Method (1) through (11) were heated to 70° C., mixed and dissolved to prepare the oil phase. Next, (12) through (17) were dispersed and mixed at 70° C. and gradually added to the oil phase while being stirred with a Disper. After thoroughly uniform mixing and stirring, the mixture was cooled to obtain the sunscreen cosmetic.

Example 9

|   | Sunscreen lotion |
|---|---|
| (1) Dimethylpolysiloxane (5 cs at 25° C.) | 10.0% |
| (2) Organofluorated modified silicone resin comprising $(CH_3)_3SiO_{1/2}/(CF_3CH_2CH_2)_2SiO/SiO_2$ wherein the content of the $(CF_3CH_2CH_2)_2SiO$ unit is 11 wt % and the weight average molecular weight is 11,100 | 15.0 |
| (3) Stearic acid | 1.0 |
| (4) Silicone type cinnamic acid derivative* | 10.0 |
| (5) Preservative | 0.2 |
| (6) Perfume | 0.2 |
| (7) Glycerine | 5.0 |
| (8) Montmorillonite | 0.5 |
| (9) Potassium hydroxide | 0.2 |
| (10) Purified water | 65.9 |

*[4-bis(trimethylsiloxy)methylsilyl-3-methylbutyl]-3,4,5-trimethoxy cinnamate

Preparation Process (1) through (6) were heated stirred at 70° C. to obtain the oil phase. (7) through (10) were heated and dissolved at 70° C. to obtain the water phase. The oil phase was added to the water phase and the resulting mixture was emulsified by an emulsifier. The emulsified product was cooled down to 30° C. by means of a heat exchanger and a container was filled to obtain the sunscreen lotion.

Each of the examples of the present invention was a cosmetic which had superior water resistance, perspiration resistance and oil resistance, and did not give a pressing feeling on the skin.

Example 10

|   | Oil type foundation |
|---|---|
| (1) Kaolin | 25% |
| (2) Titanium dioxide | 15 |
| (3) Iron oxide | 3 |
| (4) Microcrystalline wax | 4 |
| (5) Liquid paraffin | 5 |
| (6) Sorbitan sesquioleate | 1 |
| (7) Octamethylcyclotetrasiloxane | Balance |
| (8) Organofluorated modified silicone resin comprising $(CH_3)_3SiO_{1/2}/(C_4F_9CH_2CH_2)_2SiO/SiO_2$ wherein the content of the $(C_4F_9CH_2CH_2)_2SiO$ unit is 11 wt % and the weight average molecular weight is 3,270 | 10 |
| (9) Perfume | Appropriate amount |

Preparation Process (4) through (8) were stirred and dissolved at 70°–80° C., and then (1) through (3) were added to them and dispersed. After deaeration, (9) was added, a prescribed container was filled with the product to obtain the oil type foundation.

The oil-type foundation of Example 10 was a foundation with superior water resistance, oil resistance and perspiration resistance which was less susceptible to compromised makeup. Also, it did not develop cracks over time, did not cause a pressing feeling on the skin, and felt refreshing when used. After this product was stored at 50° C. for 1 month, it was stable without any aggregation or separation.

Example 11

|   | Oil type foundation |
|---|---|
| (1) Kaolin | 25% |
| (2) Titanium dioxide | 15 |
| (3) Iron oxide | 3 |
| (4) Microcrystalline wax | 4 |
| (5) Liquid paraffin | 5 |
| (6) Sorbitan sesquioleate | 1 |
| (7) Octamethylcyclotetrasiloxane | Balance |
| (8) Organofluorated modified silicone resin comprising $(CH_3)_3SiO_{1/2}/(C_8F_{19}CH_2CH_2)_2SiO/SiO_2$ wherein the content of the $(C_8F_{19}CH_2CH_2)_2SiO$ unit is 11 wt % and the weight average molecular weight is 5,500 | 10 |
| (9) Perfume | Appropriate amount |

Preparation Process (4) through (8) were stirred and dissolved at 70°–80° C., and then (1) through (3) were added to them and dispersed. After deaeration, (9) was added and a prescribed container was filled with the product to obtain the oil type foundation.

The oil-type foundation of Example 11 was a foundation with superior water resistance, oil resistance and perspiration resistance which was less susceptible to compromised makeup. Also, it did not develop cracks over time, did not cause a pressing feeling on the skin, and felt refreshing when used. After this product was stored at 50° C. for 1 month, it was stable without any aggregation or separation.

Example 12

|   | Sunscreen Cosmetic (W/O cream) |
|---|---|
| (1) Octamethylcyclotetrasiloxane | 28% |
| (2) Organofluorated modified silicone resin comprising $(CH_3)_3SiO_{1/2}/(C_4F_9CH_2CH_2)_2SiO/SiO_2$ wherein the content of the $(C_4F_9CH_2CH_2)_2SiO$ unit is 11 wt % and the weignt average molecular weight is 14,310 | 10 |
| (3) Dimethylpolysiloxane (2,500,000 cs at 25° C.) | 3.0 |
| (4) Liquid paraffin | 5.0 |
| (5) 4-methoxy-4'-t-butyldibenzoylmethane | 1.5 |
| (6) Polyether modified silicone (400 cs at 25° C.) (Polyoxyethylene group content 20 wt %) | 6.0 |
| (7) Purified water | 38.1 |
| (8) L-sodium glutamate | 3.0 |
| (9) 1,3-butyleneglycol | 5.0 |
| (10) Preservative | 0.2 |
| (11) Perfume | 0.2 |

Preparation Process (1) through (6) were mixed, heated, dissolved and the temperature of the mixture maintained at 70° C. to obtain the oil phase. Separately, (7) through (10) were heated, dissolved and the temperature of the mixture maintained at 70° C. to obtain the water phase. The water phase was added to the oil phase and the resulting mixture was thoroughly emulsified by an emulsifier. The emulsified product was stirred while being cooled. When the temperature reached 35° C. or lower, the product was poured into a container and left to stand until hard.

Example 13

| | Sunscreen Cosmetic (W/O cream) |
|---|---|
| (1) Octamethylcyclotetrasiloxane | 28% |
| (2) Organofluorated modified silicone resin comprising $(CH_3)_3SiO_{1/2}/(C_8F_{19}CH_2CH_2)_2SiO/SiO_2$ wherein the content of the $(C_8F_{19}CH_2CH_2)_2SiO$ unit is 11 wt % and the weight average molecular weight is 15,000 | 10 |
| (3) Dimethylpolysiloxane (2,500,000 cs at 25° C.) | 3.0 |
| (4) Liquid paraffin | 5.0 |
| (5) 4-methoxy-4'-t-butyldibenzoylmethane | 1.5 |
| (6) Polyether modified silicone (400 cs at 25° C.) (Polyoxyeth),Icnc group content 20 wt %) | 6.0 |
| (7) Purified water | 38.1 |
| (8) L-sodium glutamate | 3.0 |
| (9) 1,3-butyleneglycol | 5.0 |
| (10) Preservative | 0.2 |
| (11) Perfume | 0.2 |

Preparation Process (1) through (6) were mixed, heated, dissolved and the temperature of the mixture maintained at 70° C. to obtain the oil phase. Separately, (7) through (10) were heated, dissolved and the temperature of the mixture maintained at 70° C. to obtain the water phase. The water phase was added to the oil phase and the resulting mixture was thoroughly emulsified by an emulsifier. The emulsified product was stirred while being cooled. When the temperature reached 35° C. or lower, the product was poured into a container and left to stand until hard.

Example 14;

| | Liquid lip color |
|---|---|
| (1) Dimethylpolysiloxane 0.65 cs (n = 0 in Formula 1) | 25% |
| (2) Dimethylpolysiloxane 2.0 cs (n = 3 in Formula 1) | 25 |
| (3) Organofluorated modified silicone resin comprising $(CH_3)_3SiO_{1/2}/(CF_3CH_2CH_2)CH_3SiO/SiO_2$ wherein the content of the $(CF_3CH_2CH_2)CH_3SiO$ unit is 6.7 wt % and the weight average molecular weight is 11,100 | 30 |
| (4) Glyceryl triisostearate | 10 |
| (5) Red 226 | 10 |
| (6) Perfume | Appropriate amount |

Preparation Process (1) through (3) were stirred and dissolved at 70°–80° C., and (4) and (5), separately treated with a roller, were added to the mixture and dispersed. After deaeration, (6) was added to obtain the liquid lip color.

The liquid lip color of Example 14 had superior water resistance, oil resistance and perspiration resistance and was less susceptible to compromised makeup due to adhesion to a glass, for example. Also, it felt refreshing when used. Also, after this product was stored at 50° C. for 1 month, it was stable without any aggregation, separation or increased viscosity.

Example 15

| | pre-makeup |
|---|---|
| (1) Silicone-treated kaolin | 10% |
| (2) Silicone-treated titanium dioxide | 5 |
| (3) Silicone-treated red iron oxide | 0.3 |
| (4) Silicone-treated yellow iron oxide | 0.2 |
| (5) Methylphenylpolysiloxane (n = 100) | 20 |
| (6) Dimethylpolysiloxane 2 cs (n = 3 in Formula 1) | 10 |
| (7) Solid paraffin | 5 |
| (8) Microcrystalline wax | 4 |
| (9) Sorbitan sesquioleate | 1 |
| (10) Organofluorated modified silicone resin comprising $(CH_3)_3SiO_{1/2}/(CF_3CH_2CH_2)CH_3SiO/SiO_2$ wherein the content of the $(CF_3CH_2CH_2)CH_3SiO$ unit is 6.7 wt % and the weight average molecular weight is 11,100 | 2 |
| (11) Decamethylcyclopentasitoxane (n = 5 in Formula 2) | 24.5 |
| (12) Perfume | Appropriate amount |

Preparation Process (1) through (4) were mixed and crushed. Separately, (5) through (11) were mixed and dissolved at 70°–80° C. The two mixtures were stirred and mixed. After deaeration, (12) was added to obtain the pre-makeup.

The pre-makeup of Example 15 had the effect of improving the applicability of the makeup cosmetic applied on top of it and suppressing compromised makeup. After this product was stored at 50° C. for 1 month, it was stable without any aggregation, separation or increased viscosity.

Example 16

| | Sunscreen Cosmetic (W/O cream) |
|---|---|
| (1) Octamethylcyclotetrasiloxane | 28% |
| (2) Organofluorated modified silicone resin comprising $(CH_3)_3SiO_{1/2}/(CF_3CH_2CH_2)C_6H_5SiO/SiO_2$ wherein the content of the $(CF_3CH_2CH_2)C_6H_5SiO$ unit is 6.7 wt % and the weight average molecular weight is 15,000 | 10 |
| (3) Dimethylpolysiloxane (2,500,000 cs at 25° C.) | 3.0 |
| (4) Liquid paraffin | 5.0 |
| (5) 4-methoxy-4'-t-butyldibenzoylmethane | 1.5 |
| (6) Polyether modified silicone (400 cs at 25° C.) (Polyoxyethylene group content 20 wt %) | 6.0 |
| (7) Purified water | 38.1 |
| (8) L-sodium glutamate | 3.0 |
| (9) 1,3-butyleneglycol | 5.0 |
| (10) Preservative | 0.2 |
| (11) Perfume | 0.2 |

Preparation Process (1) through (6) were mixed, heated, dissolved and the temperature of the mixture maintained at 70° C. to obtain the oil phase. Separately, (7) through (10) were heated, dissolved and the temperature of the mixture maintained at 70° C. to obtain the water phase. The water phase was added to the oil phase and the resulting mixture was thoroughly emulsified by an emulsifier. The emulsified product was stirred while being cooled. When the temperature reached 35° C. or lower, the product was poured into a container and left to stand until hard.

Example 17

|  | Sunscreen Lotion |
|---|---|
| (1) Dimethylpolysiloxane (5 cs at 25° C.) | 10.0% |
| (2) Organofluorated modified silicone resin comprising $(CH_3)_3SiO_{1/2}/(CF_3CH_2CH_2)_2SiO/(CF_3CH_2CH_2)CH_3SiO/SiO_2$ wherein the content of the $(CF_3CH_2CH_2)_2SiO$ unit is 11 wt %, the content of the $(CF_3CH_2CH_2)CH_3SiO$ unit is 6.7 wt %, and the weight average molecular weight is 20,350 | 15.0 |
| (3) Stearic acid | 1.0 |
| (4) Silicone type cinnamic acid derivative* | 10.0 |
| (5) Preservative | 0.2 |
| (6) Perfume | 0.2 |
| (7) Glycerine | 5.0 |
| (8) Montmorillonite | 0.5 |
| (9) Potassium hydroxide | 0.2 |
| (10) Purified water | 65.9 |

[4-bis (trimethylsiloxy) methylsilyl-3-methylbutyl]-3,4,5-trimethoxy cinnamate

Preparation Process (1) through (6) were heated and stirred at 70° C. to obtain the oil phase. (7) through (10) were heated and dissolved at 70° C. to obtain the water phase. The oil phase was added to the water phase and the resulting mixture was emulsified by an emulsifier. The emulsified product was cooled down to 30° C. by means of a heat exchanger and poured into a container to obtain the sunscreen lotion.

Each of the examples of the present invention was a cosmetic which had superior water resistance, perspiration resistance and oil resistance, and did not give a pressing feeling on the skin.

Example 18, Example 19, Comparative Example 3, and Comparative Example 4

Powder foundations were prepared according to the formulations (quantities are in wt % units) and the secondary adhesion prevention effect was evaluated. The results are shown in Table 3.

The secondary adhesion prevention effect was determined by the lightness difference delta-Y measured by: applying 0.5 g of a sample powder foundation on a sheet of filter paper with a diameter of 5 cm; letting it stand for 15 minutes at room temperature; pasting this sheet of filter paper on a tapping apparatus; tapping 10 times a sheet of filter paper placed on the other side; and measuring the amount of transferred powder foundation to the sheet of filter paper placed on the other side using visual evaluation and a calorimeter (Minolta CM-1000).

The evaluation criteria of the visual evaluation are shown below.

⊚: No transfer is observed.
o: A small amount of transfer is observed.
Δ: More than half the amount is transferred.
X: Most of the amount is transferred.

The smaller the lightness difference ΔY is, the smaller the amount of transfer is, indicating a superior secondary adhesion prevention effect.

TABLE 3

| Powder foundation (components) | Example 18 | Example 19 | Comparative Example 3 | Comparative Example 4 |
|---|---|---|---|---|
| Organofluorated modified silicone resin (1) | 7.5 | | | |
| Organofluorated modified silicone resin (2) | | 7.5 | | |
| Organofluorated modified silicone resin (3) | | | 7.5 | |
| Trimethylsiloxysilicic acid | | | | 7.5 |
| Decamethylcyclopentasiloxane | 12.5 | 12.5 | 12.5 | 12.5 |
| Powder part (4) | 76.5 | 76.5 | 76.5 | 76.5 |
| Octylmethoxy cinnamate | 2.0 | 2.0 | 2.0 | 2.0 |
| Sorbitan sesquiisostearate | 1.5 | 1.5 | 1.5 | 1.5 |
| Total | 100.0 | 100.0 | 100.0 | 100.0 |
| Secondary adhesion prevention effect: visual evaluation | o | o | X | X |
| Secondary adhesion prevention effect: ΔY | 8 | 7 | 14 | 15 |

*Organofluorated modified silicone resin (1) comprises $(CH_3)_3SiO_{1/2}$ unit/$(CF_3CH_2CH_2)$ $CH_3SiO$ unit/$SiO_2$ unit wherein the content of the $(CF_3CH_2CH_2)$ $CH_3SiO$ unit is 6.7 wt % and the weight average molecular weight is 4,690.
*Organofluorated modified silicone resin (2) comprises $(CH_3)_3SiO_{1/2}$ unit/$(CF_3CH_2CH_2)$ $CH_3SiO$ unit/$SiO_2$ unit wherein the content of the $(CF_3CH_2CH_2)$ $CH_3SiO$ unit is 6.7 wt % and the weight average molecular weight is 20,350.
*Organofluorated modified silicone resin (3) comprises $(CH_3)_3SiO_{1/2}$ unit/$(CF_3CH_2CH_2)SiO_{3/2}$ unit/$SiO_2$ unit wherein the ratio $(CH3)_3SiO_{1/2}$ unit/{$(CF_3CH_2CH_2)SiO_{3/2}$ unit + $SiO_2$ unit} is 0.7 ant the weight average molecular weight is 12,000.
*The composition of the powder part (4) is shown below (the total is 76.5).
Talc: 12.3
Mica: 30.0
Titanium dioxide: 10.0
Yellow iron oxide: 3.0
Black iron oxide: 0.2
Red iron oxide: 1.0
Nylon powder: 10.0

Example 20, Comparative Example 5

Liquid foundations were prepared according to the formulations (quantities are in wt % unit) and the secondary adhesion prevention effect was evaluated. The results are shown in Table 4.

TABLE 41

| Liquid foundation (components) | Example 20 | Comparative Example 5 |
|---|---|---|
| Organofluorated modified silicone resin (1) | 12.5 | |
| Trimethylsiloxysilicic acid | | 12.5 |
| Decamethylcyclopentasiloxane | 38.5 | 38.5 |
| Dimethylpolysiloxane (6 cs) | 2.0 | 2.0 |
| Polyether modified silicone | 2.0 | 2.0 |
| Octylmethoxy cinnamate | 5.0 | 5.0 |
| Water repellent talc | 16.7 | 16.7 |
| Water repellent mica | 10.0 | 10.0 |
| Water repellent titanium dioxide | 10.0 | 10.0 |
| Water repellent yellow iron oxide | 2.5 | 2.5 |
| Water repellent black iron oxide | 0.1 | 0.1 |
| Water repellent red iron oxide | 0.7 | 0.7 |
| Total | 100.0 | 100.0 |
| Secondary adhesion prevention effect: visual evaluation | ⊚ | Δ |
| Secondary adhesion prevention effect: ΔY | 3 | 9 |

The cosmetic of the present invention has good water resistance, perspiration resistance and oil resistance, as well as long lasting cosmetic effects, and its film does not give a pressed feeling on the skin. Therefore, when it is made into a sunscreen cosmetic and such, the sunburn prevention effect lasts longer because it will not be washed off by serum or perspiration.

What is claimed is:

1. A cosmetic, comprising an organofluorated modified silicone resin comprising units (1), (2) and (3) as shown below:
   (1) $R_3SiO_{1/2}$ units
   (2) $SiO_2$ units
   (3) $Rf_2SiO$ units and/or RfSiO units wherein R denotes a hydrocarbon group with a carbon number of 1–6 or a phenyl group, and Rf denotes —$(CH_2)_mC_nF_{2n+1}$, m is an integer 2–4, and n is an integer 1–12, said cosmetic being selected from the group consisting of oil foundations, liquid foundations, liquid lip color, hand cream, mascara, pre-makeup, sunscreen, and powder foundations, said cosmetic further comprising at least one component selected from the group consisting of water, perfume, coloring agent(s), and powder, wherein the organofluorated modified silicone resin is blended into the cosmetic with one or more silicone oils selected from the group consisting of

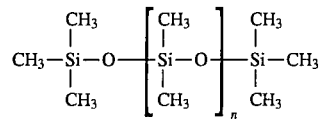

wherein n denotes an integer 0–5, and

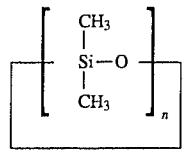

wherein n denotes an integer 3–7.

2. A method for cosmetically treating the skin comprising applying to the skin a cosmetic composition comprising an organofluorated modified silicone resin comprising units (1), (2) and (3) as shown below:
   (1) $R_3SiO_{1/2}$ units
   (2) $SiO_2$ units
   (3) $Rf_2SiO$ units and/or RfRSiO units wherein R denotes a hydrocarbon group with a carbon number of 1–6 or a phenyl group, and Rf denotes —$(CH_2)_mC_nF_{2n+1}$, m is an integer 2–4, and n is an integer 1–12.

3. A method for cosmetically treating the skin comprising applying to the skin a cosmetic composition comprising an organofluorated modified silicone resin comprising units (1), (2) and (3) as shown below:
   (1) $R_3SiO_{1/2}$ units
   (2) $SiO_2$ units
   (3) $Rf_2SiO$ units and/or RfSiO units wherein R denotes a hydrocarbon group with a carbon number of 1–6 or a phenyl group, and Rf denotes —$(CH_2)_mC_nF_{2n+1}$, m is an integer 2–4, and n is an integer 1–12, said cosmetic being selected from the group consisting of oil foundations, liquid foundations, liquid lip color, hand cream, mascara, pre-makeup, sunscreen, and powder foundations.

4. A method for cosmetically treating the skin comprising applying to the skin a cosmetic composition comprising an organofluorated modified silicone resin comprising units (1), (2) and (3) as shown below:
   (1) $R_3SiO_{1/2}$ units
   (2) $SiO_2$ units
   (3) $Rf_2SiO$ units and/or RfSiO units
wherein R denotes a hydrocarbon group with a carbon number of 1–6 or a phenyl group, and Rf denotes —$(CH_2)_mC_nF_{2n+1}$, m is an integer 2–4, and n is an integer 1–12, and further comprising at least one component selected from the group consisting of water, perfume, coloring agent(s), and powder.

* * * * *